United States Patent
Park et al.

(10) Patent No.: US 10,568,830 B2
(45) Date of Patent: Feb. 25, 2020

(54) **COMPOSITION FOR HAIR LOSS PREVENTION OR HAIR GROWTH STIMULATION COMPRISING *SCUTELLARIA ALPINA* EXTRACT**

(71) Applicant: AMOREPACIFIC CORPORATION, Seoul (KR)

(72) Inventors: Pil Joon Park, Yongin-si (KR); Seung Hyun Shin, Yongin-si (KR); Hae Kwang Lee, Yongin-si (KR); Jon Hwan Lee, Yongin-si (KR); Tae Ryong Lee, Yongin-si (KR); Eun Gyung Cho, Yongin-si (KR)

(73) Assignee: AMOREPACIFIC CORPORATION, Seoul (KR)

(*) Notice: Subject to any disclaimer, the term of this patent is extended or adjusted under 35 U.S.C. 154(b) by 40 days.

(21) Appl. No.: 15/514,600

(22) PCT Filed: Sep. 24, 2015

(86) PCT No.: PCT/KR2015/010134
§ 371 (c)(1),
(2) Date: Mar. 27, 2017

(87) PCT Pub. No.: WO2016/056780
PCT Pub. Date: Apr. 14, 2016

(65) Prior Publication Data
US 2017/0231900 A1    Aug. 17, 2017

(30) Foreign Application Priority Data
Oct. 6, 2014 (KR) .................. 10-2014-0134590

(51) Int. Cl.
| A61K 36/539 | (2006.01) |
| A61K 8/97 | (2017.01) |
| A61Q 7/00 | (2006.01) |
| A23L 33/105 | (2016.01) |
| A23L 2/52 | (2006.01) |
| A61K 8/34 | (2006.01) |

(52) U.S. Cl.
CPC .................. *A61K 8/97* (2013.01); *A23L 2/52* (2013.01); *A23L 33/105* (2016.08); *A61K 8/34* (2013.01); *A61Q 7/00* (2013.01); *A23V 2002/00* (2013.01)

(58) Field of Classification Search
None
See application file for complete search history.

(56) References Cited

U.S. PATENT DOCUMENTS

| 2006/0165636 A1 | 7/2006 | Hasebe et al. |
| 2013/0089632 A1* | 4/2013 | Kang .............. A61Q 7/00 424/770 |

FOREIGN PATENT DOCUMENTS

| JP | 01-096126 A | 4/1989 |
| KR | 10-2010-0116882 A | 11/2010 |
| KR | 10-2011-0006549 A | 1/2011 |
| KR | 10-2013-0094089 A | 8/2013 |
| WO | 2007-136773 A1 | 11/2007 |

OTHER PUBLICATIONS

Product Data Sheet: Alpoflor Scutellaria AO (available at pds5037670_06_alpaforscutellariaao.docx). Dated to Mar. 4, 2014.*
Raskin et al. (2004) Current Pharmaceutical Design, 10, 3419-3429.*
Revilla et al. (1998) J. Agric. Food Chem. 46, 4592-4597.*
Grzegorczyk-Karolak (2016) Acta. Physiol. Plant 38:7 (9 pages) (Year: 2016).*
Kim et al. (2014) Planta Med. 80: 153-158. (Year: 2014).*
Ohkoshi et al. (2009) Journal of Chromatography A, 1216: 2192-2194. (Year: 2009).*
Shin et al. (2015) Naunyn-Schmiedeberg's Arch. Pharmacol. 388: 583-586. (Year: 2015).*
International Search Report for PCT/KR2015/010134 (dated Dec. 22, 2015).
Written Opinion for PCT/KR2015/010134 (dated Dec. 22, 2015).
Alpaflor Scutellaria ao. Datasheet [online], DSM Nutritional Products Ltd, 2010, inner pp. 1-7 <Product Brochure in URL: http://www.centerchem.com/Products/alpaflor-scuttelaria-ao/>.
N.N. "Lily Shampoo record ID 1630891", Mintel GNPD database: pp. 1-3 (2011).
Search Report for European Patent Application No. 15849545.7, dated May 18, 2018.
Kim et al., "The Inhibitory Effect of Scutellaria baicalensis Extract and Its Active Compound, Bicalin, on the Translocation of the Androgen Receptor with Implications for Preventing Androgenetic Alopecia," Planta Med, 80: 153-158 (2014).
Kikuchi et al., "Studies on the Constituents of *Scutellaria* Species. XIV. On the Constituents of the Roots and the Leaves of *Scutellaria alpina* L.," Chem. Pharm. Bull. 39(1), 199-201 (1991).
Ah-Reum Kim, et al., "The Inhibitory Effect of Scutellaria baicalensis Extract and Its Active Compound, Baicalin, on the Translocation of the Androgen Receptor with Implications for Preventing Androgenetic Alopecia", Planta Med, 2014, vol. 80, pp. 153-158.
Yuichi Kikuchi, et al., "Studies on the Constituents of *Scutellaria* Species. XIV. On the Constituents of the Roots and the Leaves of *Scutellaria alpina* L.", Chem. Pharm. Buil., 1991, vol. 39, No. 1, pp. 199-201.
Office Action from Japanese Application No. 2017-518054, dated Feb. 19, 2019.

* cited by examiner

*Primary Examiner* — Russell G Fiebig
(74) *Attorney, Agent, or Firm* — Merchant & Gould P.C.

(57) ABSTRACT

Disclosed is a novel use of a composition comprising as an active ingredient a *Scutellaria alpina* extract. A composition according to the present description shows hair follicle cell proliferation or hair growth effect by means of comprising a *Scutellaria alpina* extract. Therefore, due to said effect, the *Scutellaria alpina* extract has hair loss prevention or hair growth stimulation effect.

3 Claims, 2 Drawing Sheets

COMPOSITION FOR HAIR LOSS PREVENTION OR HAIR GROWTH STIMULATION COMPRISING *SCUTELLARIA ALPINA* EXTRACT

This application is a U.S. National Stage Application under 35 U.S.C. § 371 of International Patent Application No. PCT/KR2015/010134 filed Sep. 24, 2015, which claims the benefit of priority to Korean Patent Application No. 10-2014-0134590 filed Oct. 6, 2014, the disclosures of all of which are hereby incorporated by reference in their entireties. The International Application was published in Korean on Apr. 14, 2016 as WO 2016/056780.

TECHNICAL FIELD

The present disclosure relates to a composition containing an Alpine skullcap (*Scutellaria alpina*) extract.

BACKGROUND

Whereas most animals shed and regrow hair seasonally, humans shed about 100 strands of hair out of about 100,000 strands and about 100 strands regrow every day, thus always maintaining a similar number.

The hair growth cycle consists of anagen, catagen and telogen phases. During the anagen phase, hair growth is promoted as cell division occurs actively in the hair dermal papilla and hair grows only in this stage. Considering that the anagen is about 3-5 years for men and about 4-6 years for women, about 80-85% of hair is in the anagen phase. In the catagen phase, which lasts about 3-4 weeks, the cell division declines gradually. Lastly, in the telogen phase, the hair dermal papilla is withdrawn and the hair separated from the capillary vessel and simply stuck in the scalp. This lasts about 3 months and the hair in the telogen phase is easily lost upon physical stimulation.

Although hair is not an organ critical in sustaining life, it is an indicator of health state and an important part of the body in terms of appearance. Whereas hair loss is considered a normal physiological event for those with a lot of hair, those who suffer from severe hair loss can be badly affected in terms of mental well-being and quality of life due to depression, sense of shame, social isolation, etc.

Although promotion of hair growth and prevention of hair loss have been studied from ancient times, the mechanisms of hair growth and hair loss have not been elucidated clearly yet. Recently, cytological, biochemical or molecular biological studies are actively carried out globally on hair growth and hair loss in many research institutes of universities and companies. Also, a lot of efforts are being made on the development of a drug that can treat hair loss and promote hair growth.

(Patent document 1) KR10-2010-0116882 A.

DETAILED DESCRIPTION

Technical Problem

In an aspect, the present disclosure is directed to a use for preventing hair loss or accelerating hair growth.

In another aspect, the present disclosure is directed to preventing hair loss or accelerating hair growth by promoting proliferation of hair follicle cells or growth of hair.

Technical Solution

In an aspect, the present disclosure provides a composition for preventing hair loss or accelerating hair growth, containing an extract of Alpine skullcap (*Scutellaria alpina*), which belongs to the genus *Scutellaria*, as an active ingredient.

Advantageous Effects

In an aspect, because the composition containing an Alpine skullcap (*Scutellaria alpina*) extract as an active ingredient of the present disclosure promotes proliferation of hair follicle cells or growth of hair, it can provide an effect of preventing hair loss or accelerating hair growth.

Figure 1:
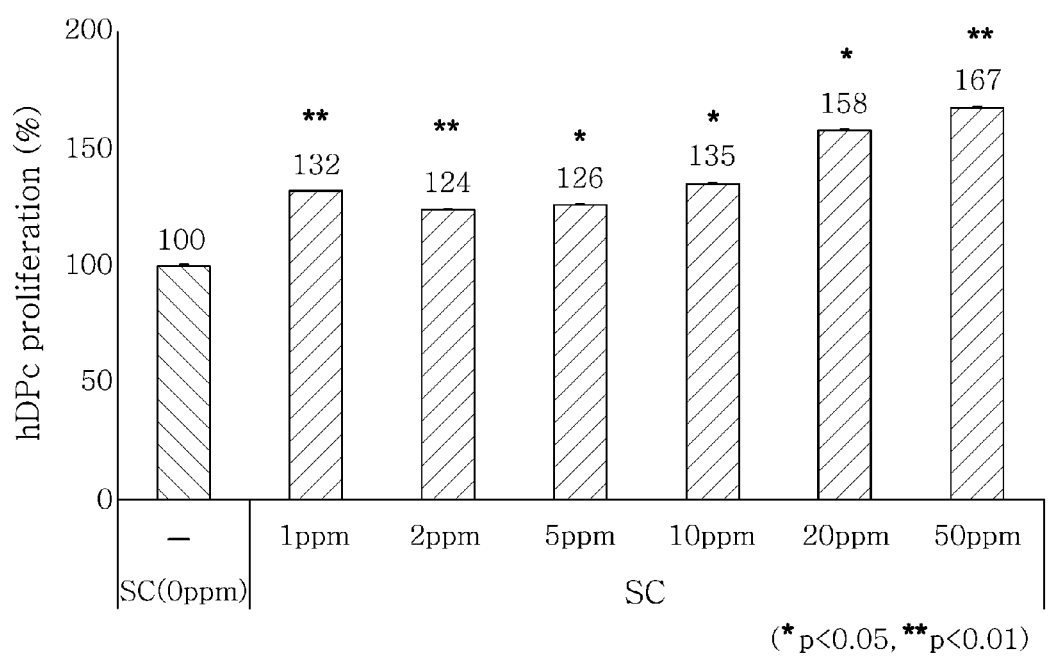
FIG. 1 shows a result of an MTT assay on hair dermal papilla cells of an Alpine skullcap (*Scutellaria alpina*) extract according to an aspect of the present disclosure (hDPc proliferation: viability of hair dermal papilla cells).

Korean Patent Application No. 10-2014-0134590, filed on Oct. 6, 2014, is incorporated herein in its entirety by reference. Also, this application claims the benefits of Korean Patent Application No. 10-2014-0134590 the contents of which in its entirety are herein incorporated by reference.

Hereinafter, specific exemplary embodiments of the present disclosure are described in detail such that those of ordinary skill in the art to which the present disclosure belongs can easily carry out the present disclosure.

In an aspect, the present disclosure may relate to a composition containing an Alpine skullcap (*Scutellaria alpina*) extract as an active ingredient. Specifically, in an aspect of the present disclosure, the composition may be a composition for preventing hair loss or accelerating hair growth.

In an aspect, the present disclosure may relate to a method for preventing hair loss or accelerating hair growth, including administering an Alpine skullcap (*Scutellaria alpina*) extract to an individual in need of prevention of hair loss or acceleration of hair growth.

In an aspect, the present disclosure may relate to a use of an Alpine skullcap (*Scutellaria alpina*) extract for hair loss prevention of hair loss or acceleration of hair growth.

In an aspect, the present disclosure may relate to an Alpine skullcap (*Scutellaria alpina*) extract for use in prevention of hair loss or acceleration of hair growth.

In an aspect of the present disclosure, the prevention of hair loss or acceleration of hair growth may be achieved by promoting proliferation of hair follicle cells or growth of hair.

In the present disclosure, the term "hair loss" may refer to absence of hair on the part where hair is normally present. For example, it may mean depilation of hair from the scalp.

And, in the present disclosure, the term "acceleration of hair growth" may refer to acceleration of not only growth of new hair but also healthy growth of existing hair.

In an aspect of the present disclosure, the prevention of hair loss or acceleration of hair growth may be achieved by promoting proliferation of hair follicle cells or growth of hair. Specifically, the proliferation of hair follicle cells may mean proliferation of hair dermal papilla cells or hair germinal matrix cells, although not being limited thereto.

In the present disclosure, the term "hair dermal papilla cell" may refer to a cell separated from the dermal cell layer and the hair dermal papilla cells may be covered with numerous hair germinal matrix cells.

And, in the present disclosure, the term "hair germinal matrix cell" may refer to a cell existing in the hair dermal papilla cell tissue and capable of producing hair.

In an aspect of the present disclosure, the Alpine skullcap (Scutellaria alpina) may be one or more selected from a group consisting of the leaf, fruit, flower, stem and root of the plant Alpine skullcap. Specifically, in an aspect of the present disclosure, the Alpine skullcap (Scutellaria alpina) may be a mixture of the flower, leaf and stem of the plant Alpine skullcap (Scutellaria alpina).

In an aspect of the present disclosure, the concentration of the Alpine skullcap (Scutellaria alpina) extract may be, based on the total weight of the composition containing the same, 0.1-70 ppm (w/w), more specifically 0.1-50 ppm (w/w), although not being limited thereto. Specifically, in an aspect of the present disclosure, the concentration of the Alpine skullcap (Scutellaria alpina) extract in the composition may be, based on the total weight of the composition, 0.1 ppm or higher, 0.5 ppm or higher, 0.6 ppm or higher, 0.7 ppm or higher, 0.8 ppm or higher, 0.9 ppm or higher, 1.0 ppm or higher, 1.3 ppm or higher, 1.5 ppm or higher, 1.7 ppm or higher, 2.0 ppm or higher, 2.3 ppm or higher, 2.5 ppm or higher, 2.7 ppm or higher, 3.0 ppm or higher, 3.5 ppm or higher, 4.0 ppm or higher, 4.1 ppm or higher, 4.2 ppm or higher, 4.3 ppm or higher, 4.4 ppm or higher, 4.5 ppm or higher, 4.6 ppm or higher, 4.7 ppm or higher, 4.8 ppm or higher, 4.9 ppm or higher, 5 ppm or higher, 5.2 ppm or higher, 5.4 ppm or higher, 5.6 ppm or higher, 5.8 ppm or higher, 6.0 ppm or higher, 6.5 ppm or higher, 7.0 ppm or higher, 7.5 ppm or higher, 8.0 ppm or higher, 9.0 ppm or higher, 10.0 ppm or higher, 11.0 ppm or higher, 12.0 ppm or higher, 20 ppm or higher, 30 ppm or higher, 40 ppm or higher, 50 ppm or higher or 60 ppm or higher, although not being limited thereto, and may be 70 ppm or lower, 60 ppm or lower, 50 ppm or lower, 40 ppm or lower, 30 ppm or lower, 20 ppm or lower, 15.0 ppm or lower, 10.0 ppm or lower, 8.0 ppm or lower, 6.0 ppm or lower, 5.8 ppm or lower, 5.6 ppm or lower, 5.4 ppm or lower, 5.2 ppm or lower, 5.0 ppm or lower, 4.8 ppm or lower, 4.6 ppm or lower, 4.4 ppm or lower, 4.2 ppm or lower, 4.0 ppm or lower, 3.7 ppm or lower, 3.5 ppm or lower, 3.3 ppm or lower, 3.0 ppm or lower, 2.8 ppm or lower, 2.6 ppm or lower, 2.4 ppm or lower, 2.2 ppm or lower, 2.0 ppm or lower, 1.8 ppm or lower, 1.6 ppm or lower, 1.4 ppm or lower, 1.2 ppm or lower, 1.0 ppm or lower, 0.8 ppm or lower, 0.6 ppm or lower or 0.3 ppm or lower. The concentration of the extract is in ppm (w/w) unit.

In an aspect of the present disclosure, the Alpine skullcap (Scutellaria alpina) extract may be prepared by a method including (1) a step of extracting Alpine skullcap (Scutellaria alpina) with water, an organic solvent or a combination thereof.

In an aspect of the present disclosure, the method may further include, before the step (1), a step of processing the Alpine skullcap (Scutellaria alpina). Specifically, the processing may be drying and then pulverizing Alpine skullcap (Scutellaria alpina) into powder. However, any processing for making extraction easier is included, without being limited thereto. The drying may be specifically sunlight drying, hot air drying, evaporation drying, spray drying or freeze-drying, more specifically hot air drying. Otherwise, in an aspect of the present disclosure, live Alpine skullcap (Scutellaria alpina) may be extracted per se without any processing.

In an aspect of the present disclosure, the method may further include a step of removing the solvent through distillation after the extraction. Specifically, the distillation may be vacuum distillation.

In an aspect of the present disclosure, the method may further include a step of adding one or more of glycerin and a preservative to the concentrate after the distillation.

In an aspect of the present disclosure, the method may further include a step of filtering after the step of removing the solvent or the step of adding one or more of glycerin and a preservative.

In an aspect of the present disclosure, the Alpine skullcap (Scutellaria alpina) extract may be an extract of one or more selected from a group consisting of water, an organic solvent and a mixture thereof. Specifically, in an aspect of the present disclosure, the organic solvent may be one or more selected from a group consisting of a $C_1$-$C_6$ lower alcohol, butylene glycol and propylene glycol. More specifically, the lower alcohol may be ethanol.

In the present disclosure, the "Alpine skullcap (Scutellaria alpina)" refers to a plant in the genus Scutellaria of the family Lamiaceae. It grows to a height of about 10-30 cm. The plant is covered with short hairs and the stems are square and prostate-ascending. The flowers are blue-violet or purple, 2.4-3 cm long. Alpine skullcap grows well in rocky areas in high calcareous mountains at elevations of 1400-2500 m.

In an aspect of the present disclosure, the term "extract" includes any substance that can be extracted from a natural product, regardless of extraction method, extraction solvent, extracted components or type of extract, and is used in a broad concept, including any substance that can be obtained by processing or treating otherwise the substance extracted from the natural product. Specifically, the processing or treatment may be fermenting or enzymatically treating the extract. Accordingly, in the present disclosure, the extract includes a fermentation product, a concentrate and a dried product. Specifically, in the present disclosure, the extract may be a fermentation product.

In an aspect of the present disclosure, the "Alpine skullcap (Scutellaria alpina) extract" includes any substance that can be extracted from Alpine skullcap (Scutellaria alpina), regardless of extraction method, extraction solvent, extracted components or type of extract and any substance obtained during the extraction process including treatment with heat, an acid, a base, an enzyme, etc., and is used in a broad concept, including any substance that can be obtained by processing or treating otherwise the substance extracted from Alpine skullcap (Scutellaria alpina). Accordingly, in an aspect of the present disclosure, the Alpine skullcap (Scutellaria alpina) extract may be a fermentation product.

In an aspect of the present disclosure, the "Alpine skullcap (Scutellaria alpina)" may be in the form of an extract, live Alpine skullcap (Scutellaria alpina), a pulverization product of live Alpine skullcap (Scutellaria alpina), a dried product of live Alpine skullcap (Scutellaria alpina), a dried pulverization product live Alpine skullcap (Scutellaria alpina) or a fermentation product of Alpine skullcap (Scutellaria alpina), although not being limited thereto. Also, the Alpine skullcap (Scutellaria alpina) used in the present disclosure is not limited as to how it is acquired. For example, it may be either cultivated or purchased commercially. Also, all or part of the areal part or root part of the herbaceous plant may be used. More specifically, one or more selected from a group consisting of the leaf, stem, root and flower of the plant Alpine skullcap (Scutellaria alpina) may be used. More specifically, flower, leaf and stem may be used. In an aspect of the present disclosure, the Alpine skullcap (*Scutellaria alpina*) needs not necessarily be dried and the form of the raw material is not limited as long as it is suitable to extract the active ingredients of Alpine skullcap (*Scutellaria alpina*).

In an aspect of the present disclosure, the water may include distilled water or purified water, and the organic solvent may include one or more selected from a group consisting of an alcohol, e.g., a $C_1$-$C_6$ lower alcohol, acetone, ether, ethyl acetate, diethyl ether, methyl ethyl ketone and chloroform, although not being limited thereto.

In an aspect of the present disclosure, the Alpine skullcap (*Scutellaria alpina*) extract may include a $C_1$-$C_6$ alcohol extract of Alpine skullcap (*Scutellaria alpina*). Specifically, the alcohol may be methanol or ethanol.

In an aspect of the present disclosure, the Alpine skullcap (*Scutellaria alpina*) extract may be obtained by a method including a step of extracting Alpine skullcap (*Scutellaria alpina*) with water, an organic solvent or a mixture thereof.

In an aspect of the present disclosure, the Alpine skullcap (*Scutellaria alpina*) extract may be a crude extract of a solvent selected from a group consisting of water, an organic solvent and a combination thereof. The organic solvent may be a $C_1$-$C_6$ alcohol. Specifically, the $C_1$-$C_6$ alcohol may be methanol or ethanol. In an aspect of the present disclosure, the Alpine skullcap (*Scutellaria alpina*) may be extracted by adding about 5-15 times, specifically about 10 times, of the solvent to Alpine skullcap (*Scutellaria alpina*), although not being limited thereto.

In an aspect of the present disclosure, the extraction may be performed by hot water extraction, ethanol extraction, heating extraction, cold precipitation extraction, reflux extraction, reflux condensation extraction, ultrasonic extraction, etc. Any extraction method obvious to those skilled in the art may be used without limitation. Specifically, the extraction may be performed by hot water extraction or ethanol extraction.

In an aspect of the present disclosure, the extraction may be performed at elevated temperatures for more effective extraction, although it may also be performed at room temperature. The extraction may be performed specifically at about 40-100° C., more specifically at about 80° C., although not being limited thereto. The extraction may be performed for about 2-14 hours, specifically for 8-14 hours, more specifically for 11-13 hours, most specifically for 12 hours. However, the extraction time may be varied depending on such conditions as extraction solvent, extraction temperature, etc. without being limited thereto. The extraction may be performed once or several times in order to obtain the active ingredients in larger quantities. The extraction may be performed specifically 1-5 times, more specifically 3 times continuously.

In an aspect of the present disclosure, the Alpine skullcap (*Scutellaria alpina*) extract may include a crude extract of Alpine skullcap (*Scutellaria alpina*) and may also include a soluble fraction obtained by further extracting the crude extract with an organic solvent of low polarity. In an aspect of the present disclosure, the organic solvent may be hexane, methylene chloride, ethyl acetate, n-butanol, etc., although not being limited thereto. The obtained extract or the soluble fraction of the extract may be used per se. Alternatively, it may be filtered and then concentrated or may be dried after the concentration.

In an aspect of the present disclosure, the drying may be evaporation drying, spray drying or freeze-drying. Specifically, freeze-drying may be performed at −50 to −70° C. for 3-4 days.

In an aspect of the present disclosure, the composition may be a cosmetic, pharmaceutical or food composition.

Specifically, the cosmetic composition may be, for example, a hair cosmetic, a body cosmetic, a foundation cosmetic, a makeup cosmetic, etc., and the formulation is not specially limited and may be selected adequately depending on purposes.

For example, the cosmetic composition may be formulated into a solution, a suspension, an emulsion, a paste, a gel, a cream, a lotion, a powder, a soap, a surfactant-containing cleanser, an oil, a powder foundation, an emulsion foundation, a wax foundation, a spray, etc., although not being limited thereto. More specifically, it may be formulated into a cleanser such as a shampoo, a rinse and a body cleanser, a hairstyling product such as a hair tonic, a gel, a mousse, etc., a hair cosmetic composition such as a hair nourisher, a hair dye, etc. or a foundation cosmetic such as a softening lotion, a nourishing lotion, a lotion, a body lotion, a nourishing cream, a massage cream, a moisturizing cream, a hand cream, an essence, an eye cream, a cleansing cream, a cleansing foam, a cleansing water, a pack, a gel, a patch, an oil-in-water (O/W) emulsion, a water-in-oil (O/W) emulsion, etc.

The cosmetic composition may contain a cosmetically acceptable medium or matrix and may be provided as any topically acceptable formulation, e.g., a solution, gel, an anhydrous solid or paste, an oil-in-water emulsion, a suspension, a microemulsion, a microcapsule, a microgranule, an ionic (liposomal) and/or nonionic vesicular dispersion, a cream, a skin lotion, a powder, an ointment, a spray or a conceal stick. The composition may be prepared according to a method commonly employed in the art.

When the formulation of the present disclosure is a solution or an emulsion, a solvent, a solubilizer or an emulsifier may be used as a carrier component. For example, water, ethanol, isopropanol, ethyl carbonate, ethyl acetate, benzyl alcohol, benzyl benzoate, propylene glycol, 1,3-butylene glycol, glycerol aliphatic ester, polyethylene glycol or a fatty acid ester of sorbitan may be used.

When the formulation of the present disclosure is a suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar or tragacanth, etc. may be used as a carrier component.

When the formulation of the present disclosure is a paste, a cream or a gel, animal oil, vegetable oil, wax, paraffin, starch, tragacanth, a cellulose derivative, polyethylene glycol, silicone, bentonite, silica, talc, zinc oxide, etc. may be used as a carrier component.

When the formulation of the present disclosure is a powder or a spray, lactose, talc, silica, aluminum hydroxide, calcium silicate or polyamide powder may be used as a carrier component. In particular, when the formulation is a spray, it may further contain a propellant such as chlorofluorohydrocarbon, propane/butane or dimethyl ether.

In an exemplary embodiment of the present disclosure, the cosmetic composition may further contain a thickener. The thickener contained in the cosmetic composition of the present disclosure may be methyl cellulose, carboxymethyl cellulose, carboxymethyl hydroxyguanine, hydroxymethyl cellulose, hydroxyethyl cellulose, carboxyvinyl polymer, polyquaternium, cetearyl alcohol, stearic acid, carrageenan, etc. Specifically, one or more of carboxymethyl cellulose, carboxyvinyl polymer and polyquaternium may be used. Most specifically, carboxyvinyl polymer may be used.

In an exemplary embodiment of the present disclosure, the cosmetic composition may contain various adequate matrices and additives as desired, and their kind and amount can be easily determined by those skilled in the art. The composition may contain acceptable additives if necessary. For example, additives commonly used in the art such as a preservative, a pigment, etc. may be contained additionally.

Specifically, the preservative may be phenoxyethanol, 1,2-hexanediol, etc. and a fragrance such as a synthetic fragrance may be used.

In an exemplary embodiment of the present disclosure, the cosmetic composition may contain a substance selected from a group consisting of a water-soluble vitamin, an oil-soluble vitamin, a polypeptide, a polysaccharide, a sphingolipid and a seaweed extract. In addition, it may further contain an oil, a fat, a humectant, an emollient, a surfactant, an organic or inorganic pigment, an organic powder, a UV absorbent, a preservative, a sterilizer, an antioxidant, a plant extract, a pH control agent, an alcohol, a colorant, a fragrance, a blood circulation stimulant, a cooling agent, an antiperspirant, purified water, etc.

However, the ingredients that may be contained in the cosmetic composition are not limited thereto and, the amount of the ingredients may be determined within a range not negatively affecting the purpose and effect of the present disclosure.

In another aspect, the present disclosure relates to a formulation for external application to skin, containing an Alpine skullcap (*Scutellaria alpina*) extract as an active ingredient. The formulation for external application to skin refers to any formulation that can be applied to skin from outside and various types of cosmetic formulations may be included therein.

In another aspect, the present disclosure relates to a pharmaceutical composition for oral or parenteral administration. Usually, the pharmaceutical composition is prepared into a formulation using a commonly used diluent or excipient such as a filler, an extender, a binder, a wetting agent, a disintegrant, a surfactant, etc. Solid formulations for oral administration may include a tablet, a pill, a powder, a granule, a soft or hard capsule, etc. The solid formulation is prepared by mixing the active ingredient with at least one excipient, e.g., starch, calcium carbonate, sucrose, lactose, gelatin, etc. In addition to the simple excipient, a lubricant such as magnesium stearate, talc, etc. may also be used. Liquid formulations for oral administration may include a suspension, a liquid medicine for internal use, an emulsion, a syrup, etc. In addition to a commonly used simple diluent such as water or liquid paraffin, various excipients such as a humectant, a sweetener, an aromatic, a preservative, etc. may also be contained. Formulations for parenteral administration may include a sterilized aqueous solution, a non-aqueous solution, a suspension, an emulsion, a freeze-dried product and a suppository. The nonaqueous solution or suspension may contain propylene glycol, polyethylene glycol, vegetable oil such as olive oil, an injectable ester such as ethyl oleate, etc. As a base of the suppository, witepsol, macrogol, tween 61, cocoa butter, laurin butter, glycerogelatin, etc. may be used.

In an aspect of the present disclosure, the active ingredient may be administered in the form of a pharmaceutically acceptable salt and may be used either alone or in combination with another pharmaceutically active compound. The salt is not particularly limited as long as it is pharmaceutically acceptable. For example, a hydrochloride, a sulfate, a nitrate, a phosphate, a hydrofluoride, a hydrobromide, a formate, an acetate, a tartrate, a lactate, a citrate, a fumarate, a maleate, a succinate, a methanesulfonate, a benzenesulfonate, a toluenesulfonate, a naphthalenesulfonate, etc. may be used.

In an aspect of the present disclosure, the composition may be administered parenterally or orally depending on purposes and a daily dosage may be 0.1-500 mg, specifically 1-100 mg, per kg body weight. The pharmaceutical composition may be administered once or several times a day. The administration dosage for a particular patient may vary depending on the body weight, age, sex and diet of the patient, administration time, administration method, excretion rate, severity of disease, etc.

The pharmaceutical composition according to an aspect of the present disclosure may be prepared into any formulation suitable for a pharmaceutical composition, including an oral formulation such as a powder, a granule, a tablet, a soft or hard capsule, a suspension, an emulsion, a syrup, an aerosol, etc., a formulation for external application to skin such as an ointment, a cream, etc., a suppository, an injection, a sterile injectable solution, etc., according to a commonly employed method. Specifically, it may be prepared into an injection or a formulation for external application to skin.

The composition according to an aspect of the present disclosure may be administered to a mammal such as rat, mouse, livestock, human, etc. through various routes including parenteral and oral routes. Any mode of administration may be expected. For example, it may be administered orally, transdermally, intravenously, intramuscularly or subcutaneously.

The composition according to an aspect of the present disclosure may be administered through various routes that can be easily adopted by those skilled in the art. In particular, the pharmaceutical composition according to an aspect of the present disclosure may be administered as a formulation for external application to skin by applying onto the skin surface.

In an aspect of the present disclosure, the composition may be a food composition. The food composition may be a health functional food composition.

The formulation of the food composition according to an aspect of the present disclosure is not particularly limited. For example, it may be formulated into a tablet, a granule, a powder, a liquid formulation such as a drink, a caramel, a gel, a bar, etc. Each formulation of the food composition may contain, in addition to the active ingredient, various ingredients commonly used in the related art. Those ingredients may be selected by those skilled in the art without difficulty in consideration of the particular formulation or purpose of use, and they may result in synergic effect when used together.

Determination of the administration dose of the active ingredient in food composition according to an aspect of the present disclosure is within the level of those skilled in the art. A daily dose may be, for example, 0.1-5000 mg/kg/day, more specifically 50-500 mg/kg/day, although not being limited thereto. The administration dose will vary depending on various factors, including the age of the subject to be treated, physical condition, presence of complication(s), or the like.

For example, the food composition according to an aspect of the present disclosure may be prepared into various foods such as a chewing gum, a caramel, a candy, a popsicle, etc., drinks such as a soft drink, mineral water, an alcoholic beverage, etc. or health functional foods including a vitamin and a mineral.

In an aspect of the present disclosure, the food composition may further contain various nutrients, vitamins, minerals (electrolytes), flavoring agents including synthetic and natural flavoring agents, colorants, extenders (cheese, chocolate, etc.), pectic acid and salts thereof, alginic acid and salts thereof, organic acids, protective colloidal thickeners, pH control agents, stabilizers, preservatives, glycerin, alcohols, carbonating agents used in soft drinks, etc. In an aspect of the present disclosure, the functional food composition may further contain a pulp for preparing a natural fruit juice, a fruit drink or a vegetable drink. These ingredients may be used either independently or in combination. The mixing ratio of the additives is of no significant importance. In an aspect of the present disclosure, the additives may be contained in an amount of about 0-20 parts by weight based on 100 parts by weight of the composition.

Hereinafter, the present disclosure will be described in detail through an example and test examples. However, the following example and test examples are for illustrative purposes only and it will be apparent to those of ordinary skill in the art that the scope of the present disclosure is not limited by the example and test examples.

[Example 1] Preparation of Alpine Skullcap (Scutellaria alpina) Extract

The flower, leaf and stem parts of Alpine skullcap (Scutellaria alpina) were harvested, hot air dried and then pulverized into a powder. The powder was extracted with an ethanol/water mixture and then ethanol was removed through vacuum distillation. After adding glycerin and a preservative to the concentrate, an Alpine skullcap (Scutellaria alpina) extract was obtained finally through filtration. The Alpine skullcap (Scutellaria alpina) extract (ALPAFLOR® SCUTELLARIA AO) prepared as described above was purchased from DSM (DSM Nutritional Products Ltd, 4002 Basel, Switzerland) and used in the following test examples.

[Test Example 1] Isolation and Culturing of Hair Follicle Cells

Hair dermal papilla cells were isolated from the human occipital scalp tissue using a microscope. The cells were cultured on a 35-mm culture dish coated with type 1 collagen for 14 days. A culture medium was replaced every 3 days. Specifically, the medium was DMEM (Dulbecco's modified Eagle's medium; Gibco BRL, Gaithersburg, Md.) containing 10 μg/mL streptomycin (Gibco, N.Y., USA), 100 u/mL penicillin (Gibco, N.Y., USA) and 20% heat-inactivated fetal bovine serum (Lonza, Walkersville, Md.). The cells were cultured in a $CO_2$ incubator under a condition of 5% $CO_2$ and 37° C.

When the hair dermal papilla cells covered 80% of the area of the plate (80% confluence), the cells were collected using 0.25% trypsin/10 mM EDTA (Gibco, N.Y., USA) and cultured further on a plate (96-well plate; Nunc, Wiebaden, Germany) containing DMEM supplemented with 10% FBS. The cells were placed on the 96-well plate at a density of 2000 cells/well and were cultured for 24 hours in a $CO_2$ incubator under a condition of 5% $CO_2$ and 37° C.

[Example 2] Measurement of Cell Proliferation (MTT Assay)

Each well of the 96-well plate was treated with an extract of Alpine skullcap (Scutellaria alpina) (0, 1, 2, 5, 10, 20, 50 ppm) for 96 hours.

After adding 70 μg/mL of an MTT solution (Sigma, St Louis, Mo.) to each well, the cells were cultured for 3 hours in a $CO_2$ incubator under a condition of 5% $CO_2$ and 37° C. Then, after adding 100 μL of DMSO (Sigma, St Louis, Mo.) to each well, absorbance was measured at 570 nm. The result is shown in FIG. 1.

As can be seen from FIG. 1, the hair dermal papilla cells treated with the Alpine skullcap (Scutellaria alpina) extract of Example 1 showed increased cell viability. The increase was statistically significant. The statistical significance was tested by the paired Student's t-test. $p<0.05$ was considered statistically significant.

[Test Example 2] Culturing of Human Hair Follicles

For experiment, 15 human hair follicle samples were taken from each group (90 samples in total).

The hair follicle samples were cultured on a 24-well plate (Nunc, Wiesbaden, Germany) containing 500 μL of William's E medium (Gibco, N.Y., USA) containing 2 mM L-glutamine (PAA, Coelbe, Germany), 10 μg/mL insulin, 10 ng/mL hydrocortisone (Sigma, St Louis, Mo.), 0.1% fungizone (Gibco, N.Y., USA), 10 μg/mL streptomycin and 100 u/mL penicillin (Gibco, N.Y., USA), with 5-6 samples per well.

[Example 3] Observation of Growth of Hair Follicles

The 24-well plate was treated with an extract of Alpine skullcap (Scutellaria alpina) (0, 10, 50 ppm). A sample not treated with Alpine skullcap (Scutellaria alpina) was used as a control group. The medium was replaced every 2-3 days.

After treating with the Alpine skullcap (Scutellaria alpina) extract, the hair follicles were imaged using a stereoscopic microscope (Dongwon CNS, Korea) and hair growth length was measured using the ImageJ program. The result is shown in FIG. 2.

Figure 2:
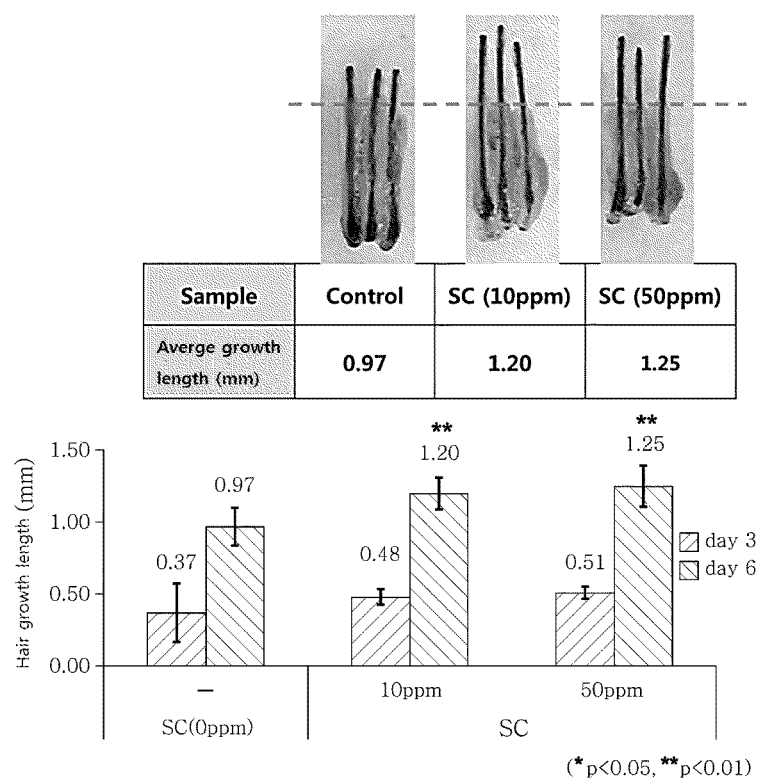
FIG. 2 shows the effect of Alpine skullcap (*Scutellaria alpina*) extract according to an aspect of the present disclosure on hair growth.

As can be seen from FIG. 2, the group treated with the Alpine skullcap (Scutellaria alpina) extract showed a longer average growth length and a larger hair follicle volume.

Hereinafter, the formulation examples of the composition according to an aspect of the present disclosure are described. However, the following formulation examples are for illustrative purposes only and do not limit the scope of the present disclosure.

[Formulation Example 1] Soft Capsule 8 mg of the Alpine skullcap (Scutellaria alpina) extract of Example 1, 9 mg of vitamin E, 9 mg of vitamin C, 2 mg of palm oil, 8 mg of hydrogenated vegetable oil, 4 mg of yellow beeswax and 9 mg of lecithin were mixed and prepared into a soft capsule-filling solution according to a commonly employed method. A soft capsule was prepared by filling 400 mg of the solution per capsule. Separately from this, a soft capsule sheet was prepared from 66 parts by weight of gelatin, 24 parts by weight of glycerin and 10 parts by weight of a sorbitol solution and filled with the filling solution to prepare a soft capsule containing 400 mg of the composition according to an aspect of the present disclosure.

[Formulation Example 2] Tablet 8 mg of the Alpine skullcap (Scutellaria alpina) extract of Example 1, 9 mg of vitamin E, 9 mg of vitamin C, 200 mg of galactooligosaccharide, 60 mg of lactose and 140 mg of maltose were mixed and granulated using a fluidized-bed drier. After adding 6 mg of sugar ester, 500 mg of the resulting composition was prepared into a tablet according to a commonly employed method.

[Formulation Example 3] Drink 8 mg of the Alpine skullcap (*Scutellaria alpina*) extract of Example 1, 9 mg of vitamin E, 9 mg of vitamin C, 10 g of glucose, 0.6 g of citric acid and 25 g of oligosaccharide syrup were mixed with 300 mL of purified water. 200 mL of the resulting drink was filled in a bottle and sterilized at 130° C. for 4-5 seconds.

[Formulation Example 4] Granule 8 mg of the Alpine skullcap (*Scutellaria alpina*) extract of Example 1, 9 mg of vitamin E, 9 mg of vitamin C, 250 mg of anhydrous crystalline glucose and 550 mg of starch were mixed and granulated using a fluidized-bed drier. The prepared granule was filled in a pouch.

[Formulation Example 5] Injection

An injection was prepared with the composition described in Table 1 according to a commonly employed method.

TABLE 1

| Ingredients | Contents |
|---|---|
| Alpine skullcap (*Scutellaria alpina*) extract of Example 1 | 10-50 mg |
| Sterilized distilled water for injection | adequate |
| pH control agent | adequate |

[Formulation Example 6] Health Functional Food

A health functional food was prepared with the composition described in Table 2 according to a commonly employed method.

TABLE 2

| Ingredients | Contents |
|---|---|
| Alpine skullcap (*Scutellaria alpina*) extract of Example 1 | 20 mg |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |
| Potassium citrate | 90 mg |
| Calcium carbonate | 100 mg |
| Magnesium chloride | 24.8 mg |

Although the above-described composition of the vitamin and mineral mixtures is given as a specific example adequate for a health functional food, it may be altered otherwise.

[Formulation Example 7] Health Drink

A health drink was prepared with the composition described in Table 3 according to a commonly employed method.

TABLE 3

| Ingredients | Contents |
|---|---|
| Alpine skullcap (*Scutellaria alpina*) extract of Example 1 | 1000 mg |
| Citric acid | 1000 mg |
| Oligosaccharide | 100 g |
| Taurine | 1 g |
| Purified water | balance |

The above ingredients were mixed and heated for about 1 hour at 85° C. while stirring according to a commonly employed health drink preparation method. The resulting solution was filtered and sterilized.

[Formulation Example 8] Shampoo

A shampoo was prepared with the composition described in Table 4 according to a commonly employed method.

TABLE 4

| Ingredients | Contents (wt %) |
|---|---|
| Alpine skullcap (*Scutellaria alpina*) extract of Example 1 | 0.2 |
| Ammonium laureth sulfate | 10.0 |
| Glycol distearate | 2.0 |
| Cetyl alcohol | 0.6 |
| Cocamide MEA | 0.5 |
| Ammonium lauryl sulfate | 6.0 |
| Guar hydroxypropyltrimonium chloride | 0.15 |
| Polyquaternium-10 | 0.1 |
| Silicone | 0.5 |
| Distearyldimethylammonium chloride | 0.2 |
| Sodium cocoamphoacetate | 4.0 |
| Fragrance | 1.0 |
| Preservative | 0.03 |
| Citric acid | adequate |
| Purified water | balance |

[Formulation Example 9] Rinse

A rinse was prepared with the composition described in Table 5 according to a commonly employed method.

TABLE 5

| Ingredients | Contents (wt %) |
|---|---|
| Alpine skullcap (*Scutellaria alpina*) extract of Example 1 | 0.2 |
| Cetyl alcohol | 3.0 |
| Glycerin monostearate | 1.0 |
| Hydroxyethyl cellulose | 1.0 |
| Propylene glycol | 4.0 |
| Methyl parahydroxybenzoate | 0.2 |
| Stearyldimethylbenzylammonium chloride, 25% | 10.0 |
| Fragrance | adequate |
| Pigment | adequate |
| Citric acid | adequate |
| Purified water | balance |

[Formulation Example 10] Ointment

An ointment was prepared with the composition described in Table 6 according to a commonly employed method.

TABLE 6

| Ingredients | Contents (wt %) |
|---|---|
| Alpine skullcap (*Scutellaria alpina*) extract of Example 1 | 0.2 |
| Butylene glycol | 4.0 |
| Liquid paraffin | 15.0 |
| Beta-glucan | 7.0 |
| Carbomer | 0.1 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |
| Glycerin | 8.0 |
| Preservative, pigment and fragrance | adequate |
| Purified water | balance |

[Formulation Example 11] Massage Cream

A massage cream was prepared with the composition described in Table 7 according to a commonly employed method.

TABLE 7

| Ingredients | Contents (wt %) |
|---|---|
| Alpine skullcap (*Scutellaria alpina*) extract of Example 1 | 2.0 |
| Glycerin | 8.0 |
| Butylene glycol | 4.0 |
| Liquid paraffin | 45.0 |
| Beta-glucan | 7.0 |
| Carbomer | 0.1 |
| Caprylic/capric triglyceride | 3.0 |
| Beeswax | 4.0 |
| Cetearyl glucoside | 1.5 |
| Sorbitan sesquioleate | 0.9 |
| Vaseline | 3.0 |
| Paraffin | 1.5 |
| Preservative, pigment and fragrance | adequate |
| Purified water | balance |

[Formulation Example 12] Hair Pack

A hair pack was prepared with the composition described in Table 8 according to a commonly employed method.

TABLE 8

| Ingredients | Contents (wt %) |
|---|---|
| Alpine skullcap (*Scutellaria alpina*) extract of Example 1 | 0.2 |
| Glycerin | 4.0 |
| Polyvinyl alcohol | 15.0 |
| Hyaluronic acid extract | 5.0 |
| Beta-glucan | 7.0 |
| Allantoin | 0.1 |
| Nonyl phenyl ether | 0.4 |
| Polysorbate 60 | 1.2 |
| Ethanol | 6.0 |
| Preservative, pigment and fragrance | adequate |
| Purified water | balance |

[Formulation Example 13] Softening Lotion (Skin Lotion)

A softening lotion was prepared with the composition described in Table 9 according to a commonly employed method.

TABLE 9

| Ingredients | Contents (wt %) |
|---|---|
| Alpine skullcap (*Scutellaria alpina*) extract of Example 1 | 0.2 |
| Glycerin | 3.0 |
| Butylene glycol | 2.0 |
| Propylene glycol | 2.0 |
| Carboxyvinyl polymer | 0.1 |
| PEG-12 nonyl phenyl ether | 0.2 |
| Polysorbate 80 | 0.4 |
| Ethanol | 10.0 |
| Triethanolamine | 0.1 |
| Preservative, pigment and fragrance | adequate |
| Purified water | balance |

[Formulation Example 14] Nourishing Lotion (Milk Lotion)

A nourishing lotion was prepared with the composition described in Table 10 according to a commonly employed method.

TABLE 10

| Ingredients | Contents (wt %) |
|---|---|
| Alpine skullcap (*Scutellaria alpina*) extract of Example 1 | 1.0 |
| Glycerin | 3.0 |
| Butylene glycol | 3.0 |
| Propylene glycol | 3.0 |
| Carboxyvinyl polymer | 0.1 |
| Beeswax | 4.0 |
| Polysorbate 60 | 1.5 |
| Caprylic/capric triglyceride | 5.0 |
| Squalane | 5.0 |
| Sorbitan sesquioleate | 1.5 |
| Liquid paraffin | 0.5 |
| Cetearyl alcohol | 1.0 |
| Triethanolamine | 0.2 |
| Preservative, pigment and fragrance | adequate |
| Purified water | balance |

While the exemplary embodiments have been shown and described, it will be understood by those skilled in the art that various changes in form and details may be made thereto without departing from the spirit and scope of this disclosure as defined by the appended claims.

We claim:

1. A method for promoting proliferation of hair follicle cells in a subject having hair loss, comprising topically administering to an area in need thereof an effective amount of a composition comprising a hydro-ethanolic extract of Alpine skullcap (*Scutellaria alpina*),
    wherein the composition comprises at least 0.2 wt % of the extract, and
    wherein the composition is a cosmetic composition or pharmaceutical composition.

2. The method according to claim 1, wherein the hair follicle cell is a hair dermal papilla cell or a hair germinal matrix cell.

3. The method according to claim 1, wherein the Alpine skullcap is one or more selected from a group consisting of a leaf, a flower, a stem and a root of the Alpine skullcap.

* * * * *